(12) United States Patent
McSwain et al.

(10) Patent No.: US 8,426,638 B2
(45) Date of Patent: Apr. 23, 2013

(54) USE OF PREDEHYDRATION TOWERS IN AN ETHANE OXIDATION TO ACETIC ACID/ETHYLENE PROCESS

(75) Inventors: C. V. McSwain, Corpus Christi, TX (US); George C. Seaman, Corpus Christi, TX (US)

(73) Assignee: Celanese International Corp., Irving, TX (US)

( * ) Notice: Subject to any disclaimer, the term of this patent is extended or adjusted under 35 U.S.C. 154(b) by 451 days.

(21) Appl. No.: 12/223,205

(22) PCT Filed: Jan. 30, 2007

(86) PCT No.: PCT/US2007/002636
§ 371 (c)(1),
(2), (4) Date: Jun. 11, 2010

(87) PCT Pub. No.: WO2007/092225
PCT Pub. Date: Aug. 16, 2007

(65) Prior Publication Data
US 2010/0249456 A1    Sep. 30, 2010

Related U.S. Application Data

(60) Provisional application No. 60/765,988, filed on Feb. 7, 2006.

(51) Int. Cl.
*C07C 51/16* (2006.01)
(52) U.S. Cl.
USPC ............................................ 562/549; 562/548
(58) Field of Classification Search .................. 562/548, 562/543, 544, 549
See application file for complete search history.

(56) References Cited

U.S. PATENT DOCUMENTS

| | | | | |
|---|---|---|---|---|
| 5,492,603 A | * | 2/1996 | Gualy et al. | 202/158 |
| 6,913,734 B2 | * | 7/2005 | Becker et al. | 422/139 |
| 7,015,355 B2 | * | 3/2006 | Zeyss et al. | 562/548 |

FOREIGN PATENT DOCUMENTS

WO   WO02/30861   *   4/2002

* cited by examiner

*Primary Examiner* — Taylor Victor Oh
(74) *Attorney, Agent, or Firm* — Michael W. Ferrell

(57) ABSTRACT

Described herein is a process in which acetic acid is produced by ethane oxidation. One byproduct of the ethane oxidation is water, which is commonly removed from the process in the same stream as the acetic acid process. As described herein, the ethane oxidation reactor effluent is processed in a predehydration tower so as to separately recover water, acetic acid, and a gas stream for recycle back to the ethane oxidation reactor.

23 Claims, 2 Drawing Sheets

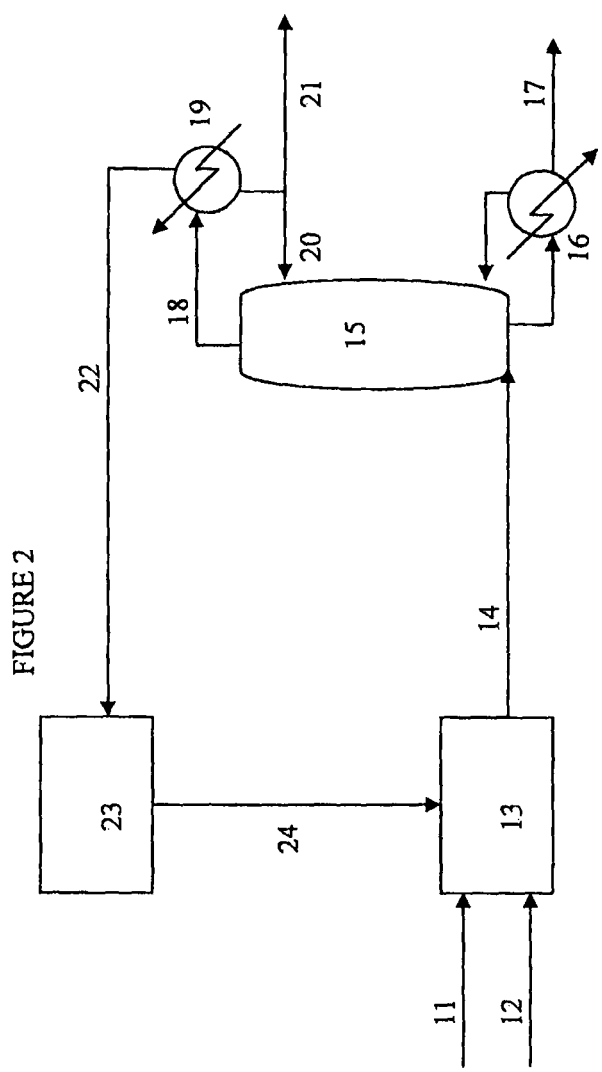

USE OF PREDEHYDRATION TOWERS IN AN ETHANE OXIDATION TO ACETIC ACID/ETHYLENE PROCESS

FIELD OF THE INVENTION

This invention relates to the process of oxidizing ethane to produce acetic acid. In particular, this invention relates to a method of oxidizing ethane to acetic acid wherein acetic acid is recovered from the oxidation reactor product stream using predehydration towers.

BACKGROUND OF THE INVENTION

The oxidative dehydrogenation of ethane to acetic acid and ethylene in the gas phase is well known in the art. Generally, this process involves reacting a gaseous feed in a fluidized bed or in a fixed-bed reactor. The gaseous feed comprises ethane and/or ethylene which are fed to the reactor as pure gases or in admixture with one or more other gases. Examples of such additional, or carrier, gases are nitrogen, methane, carbon monoxide, carbon dioxide, air and/or water vapor. The gas comprising molecular oxygen can be air or a gas comprising more or less molecular oxygen than air, e.g. oxygen. Relatively high oxygen contents are preferred since the achievable ethane conversion, and thus the yield of acetic acid, is higher. Oxygen or the gas comprising molecular oxygen is preferably added in a concentration range outside the explosive limits under the reaction conditions since this makes the process easier to carry out. However, it is also possible to employ an ethane/ethylene to oxygen ratio within the explosive limits. The reaction is carried out at temperatures of from 400 to 600° C., while the pressure can be atmospheric or superatmospheric, e.g. in the range from 1 to 50 bar.

Ethane is usually first mixed with the inert gases such as nitrogen or water vapor before oxygen or the gas comprising molecular oxygen is fed in. The mixed gases are preferably preheated to the reaction temperature in a preheating zone before the gas mixture is brought into contact with the catalyst. Acetic acid is usually separated from the gas leaving the reactor by condensation. The remaining gases are recirculated to the reactor inlet where oxygen or the gas comprising molecular oxygen and also ethane and/or ethylene are metered in. The recirculated gases will always comprise both ethylene and ethane.

FIG. 1 shows a common prior art acetic acid production process. In this basic system, an ethane containing stream (1) is fed along with an oxygen containing gas (2) into an ethane oxidation reactor (3). This reactor can be either a fluidized bed or fixed-bed reactor. Inside the reactor (3), ethane is oxidized into acetic acid, ethylene, and various carbon oxides ($CO_x$). The gaseous reactor effluent (4) that contains these three primary components is fed into a recycle gas scrubber (5), which produces a top stream containing ethylene, ethane, and $CO_x$. The top stream (7) from the recycle gas scrubber is routed to a processing step (8) that removes the $CO_x$ from the top stream. The purified stream (9) is then recycled to the oxidation reactor (3) for further conversion into acetic acid. The bottom stream (6) from the recycle gas scrubber (5), which contains acetic acid, water, and heavy ends by-products, may be purified as known in the art to provide purified acetic acid. For example, the bottom stream may be routed to a drying column to remove water followed by a heavy ends column to remove propionic acid and other heavy components.

Often times the ethane oxidation reactor effluent will exit the reactor at a high temperature and contain large quantities of water. Water would ultimately need to be separated from the process, and as described above, the water is often removed from the process in the same stream as the acetic acid, and is then subject to further processing to remove the water. It would therefore be beneficial to develop a process wherein acetic acid can be recovered separately from the water in the effluent of an ethane oxidation to acetic acid reactor, thereby eliminating a further water removal step.

SUMMARY OF THE INVENTION

It is an object of this invention to provide a process in which acetic acid is produced by ethane oxidation. One byproduct of the ethane oxidation, water, is normally removed from the reactor effluent with the acetic acid. In one object of the invention, the reactor effluent is processed in a predehydration tower so as to separately recover water, acetic acid, and a gas stream for recycle back to the ethane oxidation reactor.

BRIEF DESCRIPTION OF THE DRAWINGS

FIG. 2 shows one embodiment of the acetic acid production process of the present invention.

DETAILED DESCRIPTION OF THE INVENTION

Figure 1:
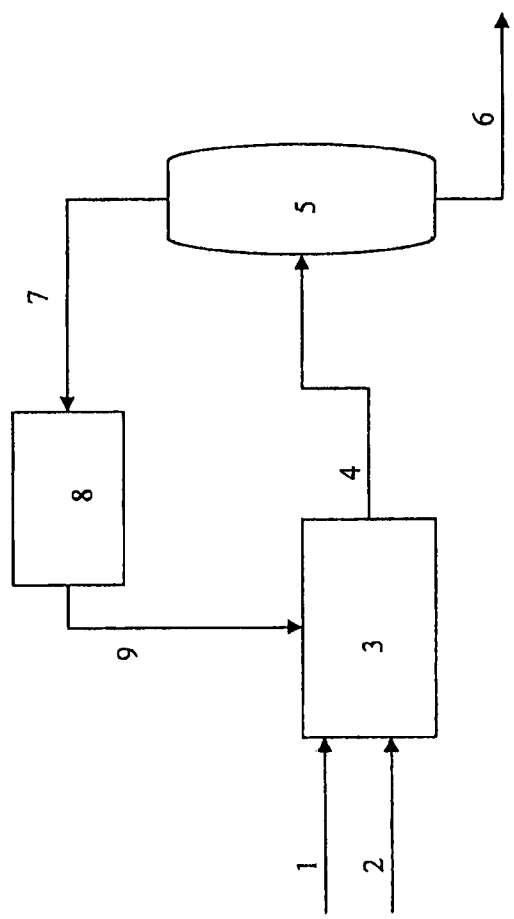
FIG. 1 shows a prior art acetic acid production process.

The present invention provides a process for selectively preparing acetic acid from the oxidation of ethane. One byproduct of the ethane oxidation reaction is water, and it is an objective of this application to recover dry acetic acid from this process using predehydration towers.

The oxidation of ethane can be carried out in a fluidized bed or in a fixed bed reactor. For use in a fluidized bed, the catalyst is normally ground to a particle size in the range from 10 to 200 µm or prepared by spray drying.

The gaseous feedstock, and any recycle gas combined with said feedstock gas, contains primarily ethane, but may contain some amount of ethylene, and is fed to the reactor as a pure gas or in a mixture with one or more other gases. Suitable examples of such additional or carrier gases are nitrogen, methane, carbon monoxide, carbon dioxide, air and/or steam. The gas containing molecular oxygen may be air or a gas which has a higher or lower molecular oxygen concentration than air, for example pure oxygen. The ethane oxidation reaction is generally carried out at about 400 to about 600° C., preferably about 450 to about 550° C., the key being that the temperature be high enough to oxidize ethane. The appropriate temperature will depend upon the catalyst used in the ethane oxidation reactor. There are a wide range of catalysts for use in this reaction, and one of ordinary skill in the art will know how to optimize catalyst performance by finding the appropriate reaction temperature. The pressure can be atmospheric or superatmospheric, for example about 1 to about 50 bar, preferably about 1 to about 30 bar.

The oxidation reaction produces a mixture of gases including ethylene, acetic acid, water, $CO_x$ (CO and $CO_2$), unreacted ethane, and assorted heavy by-products. This product gas normally exits the reactor at a temperature between about 450 to about 600° C. The product gas effluent from the reactor is then preferably filtered to remove catalyst fines and is then routed to a predehydration tower.

The reactor effluent enters the base of the predehydration tower, and due to the high temperature of the stream, provides most, if not all, of the energy necessary to effectuate the separation of acetic acid from water in the tower. Alternatively, a reboiler at the base of the predehydration tower could be used to provide additional energy input into the tower. The tower would operate at or near the pressure of the ethane oxidation reactor, and would preferably contain 25-35 stages, however the number of stages can vary depending upon the quality of the separation desired. An overhead condensing system cools the overhead gas stream to a temperature below the condensation point of the water vapor, preferably about 100-120° C., and would provide reflux to the predehydration tower. An overhead liquid water product is recovered, this water having very low levels of acetic acid therein, preferably less than 1%, allowing for that stream to be disposed of biologically. Such disposal methods are known in the art. The bottoms stream from the predehydration tower is crude acetic acid with much lower water content, preferably less than 10% water, than had the stream been processed in a conventional stripper. The gaseous top stream from the predehydration tower is routed to a fixed bed CO converter followed by a processing step that removes the $CO_x$ from the top stream. This purified stream is then recycled to the ethane oxidation reactor for further conversion into acetic acid.

One of skill in the art will appreciate that the towers, scrubbers, and routing referred to in the preceding paragraphs will have associated with them various heat exchangers, pumps, and connectors and will have operating parameters that are determined by the particular mixture of gases involved. It is within the ability of one of ordinary skill in the art to determine the proper configurations and parameters, given the above disclosure.

FIG. 2 shows one embodiment of the present invention. In this embodiment, the gaseous ethane feedstock (11) and any recycle gas (24) are fed to the ethane oxidation reactor (13) as a pure gas or in a mixture with one or more carrier gases described above. An oxygen containing gas (12) is also fed to the reactor (13). The ethane oxidation reaction temperature is generally carried out at about 400 to about 600° C., preferably about 450 to about 550° C., depending on the catalyst used, the key being that the temperature be high enough to oxidize ethane. The appropriate temperature will depend upon which of the numerous available catalysts are used in the ethane oxidation reactor. Such a temperature determination is within the skill of one of ordinary skill in the art.

The oxidation reaction produces a mixture of gases (14) that includes ethylene, acetic acid, water, $CO_x$, unreacted ethane, and assorted heavy by-products. The ethane oxidation product gas (14) is then introduced into the bottom of a predehydration tower (15). A reboiler (16) is provided, but may not be necessary depending upon the temperature of the reactor outlet stream (14), at the base of the predehydration tower to provide additional energy input into the tower by heating the bottoms stream. The bottoms stream of the predehydration tower, containing primarily acetic acid, would be heated in the reboiler (16), vaporizing part of the stream for reintroduction in to the predehydration tower (15). The balance of the bottoms stream, the crude acetic acid stream (17) is removed from the system and sent downstream for further processing.

An overhead condensing system (19) cools the overhead gas stream (18), and provides a liquid reflux (20) to the predehydration tower (15). An overhead liquid water product (21) is recovered, containing very low levels of acetic acid. This water stream (21) would then be sent on for further processing, cleanup and/or disposal. The gaseous top stream (22) from the predehydration tower, containing primarily unreacted ethane, ethylene, and $CO_x$ gasses, is then routed to a fixed bed CO converter followed by a processing step that removes the $CO_x$ from the top stream (23). This purified stream (24) is then recycled to the ethane oxidation reactor (13) for further conversion into acetic acid.

The preceding description is set forth for purposes of illustration only and is not to be taken in a limited sense. Various modifications and alterations will be readily apparent to persons skilled in the art. It is intended, therefore, that the foregoing be considered as exemplary only and that the scope of the invention be ascertained from the following claims.

The invention claimed is:

1. A process for the production of acetic acid, comprising:
   oxidizing ethane in an ethane oxidation reactor to form a gaseous product stream comprising water, acetic acid, and ethane, and
   feeding the gaseous product stream directly to a tower to separately recover a bottoms stream comprising at least 90 percent acetic acid, a water stream comprising less than 1 percent acetic acid, and a gas stream comprising ethylene and unreacted ethane, wherein the gaseous product stream is fed to the tower at an elevated temperature such that due to the high temperature of the stream, the stream provides energy necessary to effectuate the separation of acetic acid from water in the tower.

2. The process of claim 1, wherein the product stream flows through a filter after the oxidizing step and before the processing step.

3. The process of claim 1, wherein the pressure of the predehydration tower is about 1 bar to about 50 bar.

4. The process of claim 1, wherein the processing step comprises providing additional energy input into the tower by using a reboiler.

5. The process of claim 1, wherein the processing comprises cooling the gas stream with an overhead condensing system.

6. The process of claim 5, wherein the gas stream is cooled to about 100° C. to about 120° C.

7. The process of claim 1, wherein the oxidizing step is performed at about 400° C. to about 600° C.

8. The process of claim 1, wherein the oxidizing step utilizes a carrier gas.

9. The process of claim 8, wherein the carrier gas is selected form the group consisting of nitrogen, methane, carbon monoxide, carbon dioxide, air, steam, and a combination thereof.

10. The process of claim 1, wherein the pressure of the oxidation reactor is about 1 bar to about 50 bar.

11. A process for the production of acetic acid, comprising:
   oxidizing ethane in an ethane oxidation reactor to form a gaseous product stream comprising water, acetic acid, and ethane, at an elevated temperature between about 450° C. and about 600° C. and
   feeding the gaseous product stream to a tower to separately recover a bottoms stream comprising acetic acid, a water stream comprising less than 1 percent acetic acid, and a gas stream comprising ethylene and unreacted ethane, wherein the gaseous product stream is fed to the tower at the elevated temperature such that due to the high temperature of the stream, the stream provides energy necessary to effectuate the separation of acetic acid from water in the tower.

12. The method of claim 11, carried out in an apparatus for manufacturing acetic acid, including:
   an ethane oxidation reactor in communication with an ethane source, an oxygen source, a recycle stream, and a gaseous outlet product stream;
   a predehydration tower in communication with the gaseous outlet product stream and an overhead condensing system, wherein the predehydration tower is adapted to separately recover a bottoms stream containing acetic acid, a water stream and an overhead gas stream; and
a $CO_x$ converter in communication with the overhead gas stream and the recycle stream.

13. The method of claim 12, wherein the overhead condensing system is in communication with an overhead recycle stream, reflux stream, and water stream.

14. The method of claim 13, wherein the condensing system comprises a condenser which has an operating temperature of about 100° C. to about 120° C.

15. The method of claim 12, wherein the predehydration tower further comprises a reboiler in communication with the predehydration tower, a reboiler reflux stream, and an acetic acid stream.

16. The method of claim 15, wherein the reboiler has an operating temperature that is high enough to vaporize part of the reboiler reflux stream.

17. The method of claim 12, wherein the predehydration tower has 25-35 stages.

18. The method according to claim 11, carried out in an apparatus for manufacturing acetic acid, including:
an ethane oxidation reactor in communication with an ethane source, an oxygen source, a recycle stream, and a gaseous outlet product stream;
a predehydration tower in communication with the gaseous outlet product stream, an acetic acid stream, and an overhead gas stream, wherein the predehydration tower is adapted to separately recover a bottoms stream containing acetic acid, a water stream and an overhead gas stream;
a condenser in communication with the overhead gas stream; and
a reboiler in communication with the acetic acid stream.

19. The method according to claim 18, wherein the apparatus further comprises a $CO_x$ converter in communication with the overhead gas stream and the recycle stream.

20. The method according to claim 11, carried out in an apparatus for manufacturing acetic acid, including:
means for oxidizing ethane to produce a gaseous product stream comprising water, acetic acid, and ethane; and
means for processing the gaseous product stream to separately recover a bottoms stream comprising at least 90 percent acetic acid, a water stream comprising less than 1 percent acetic acid, and a gas stream comprising ethylene and unreacted ethane.

21. The method according to claim 20, wherein the means for processing comprises a reboiler in communication with the predehydration tower, a reboiler reflux stream, and an acetic acid stream.

22. The process of claim 1 wherein the gaseous product stream exits the reactor at a temperature between about 450° and about 600° C.

23. The process of claim 22, wherein the product stream comprises ethylene, acetic acid, water, CO, $CO_2$ and unreacted ethane.

* * * * *